US012806200B1

(12) United States Patent
Almarzooqi et al.

(10) Patent No.: US 12,806,200 B1
(45) Date of Patent: Nov. 24, 2026

(54) PHARMACEUTICAL COMPOSITION COMPRISING BICYCLIC COMPOUNDS FOR USE AS ENERGY BOOSTERS

(71) Applicant: United Arab Emirates University, Al Ain (AE)

(72) Inventors: Ahmed Almarzooqi, Al Ain (AE); Alya A. Arabi, Al Ain (AE); Amira Bekdash, Al Ain (AE); Jisha Chalissery, Al Ain (AE); Tiyyaba Furqan, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 19/315,102

(22) Filed: Aug. 29, 2025

(51) Int. Cl.
*A61K 31/517* (2006.01)
*A61K 9/48* (2006.01)
*A61K 31/7076* (2006.01)

(52) U.S. Cl.
CPC .......... *A61K 31/517* (2013.01); *A61K 9/4808* (2013.01); *A61K 31/7076* (2013.01)

(58) Field of Classification Search
CPC .......................... A61K 31/517; A61K 31/7076
See application file for complete search history.

(56) References Cited

FOREIGN PATENT DOCUMENTS

WO WO-2015112739 A1 * 7/2015 ........... C07D 413/14
WO WO-2020142748 A1 * 7/2020 ........... C07D 519/00

OTHER PUBLICATIONS

Ambudkar, S. V. Methods Enzymol. 1998:292:504-14. (Year: 1998).*
Healy, A. M., et al. Advanced Drug Delivery Reviews. 117, 2017, 25-46. (Year: 2017).*
Rautio, J., et al. Nature Reviews Drug Discovery. 17, 2018, 559-587. (Year: 2018).*
Kim, H. G., et al. Toxicology Reports. 9, (2022), 1883-1893. (Year: 2022).*
Cai, C, Y., et al. Biomolecules. 2023, 13, 253. (Year: 2023).*
Vinkurov, A. Y., et al. Current Research in Pharmacology and Drug Discovery 6 (2024) 100187. (Year: 2024).*

* cited by examiner

*Primary Examiner* — Andrea Olson
*Assistant Examiner* — Samuel L Galster
(74) *Attorney, Agent, or Firm* — MH2 Technology Law Group, LLP

(57) ABSTRACT

The present invention relates to a pharmaceutical composition comprising a therapeutically effective amount of a compound of Formula (I), along with their corresponding dosage forms, and use of these compounds to directly catalyzing ATP hydrolysis without requiring any enzymes to boost energy production. Furthermore, the present invention provides a method for treating or preventing diseases, conditions or disorders associated with impaired cellular bioenergetics or for enhancing cellular energy (e.g. by providing an energy boost) by administering a therapeutically effective amount of the compound of Formula (I) to a subject in need thereof.

17 Claims, 1 Drawing Sheet

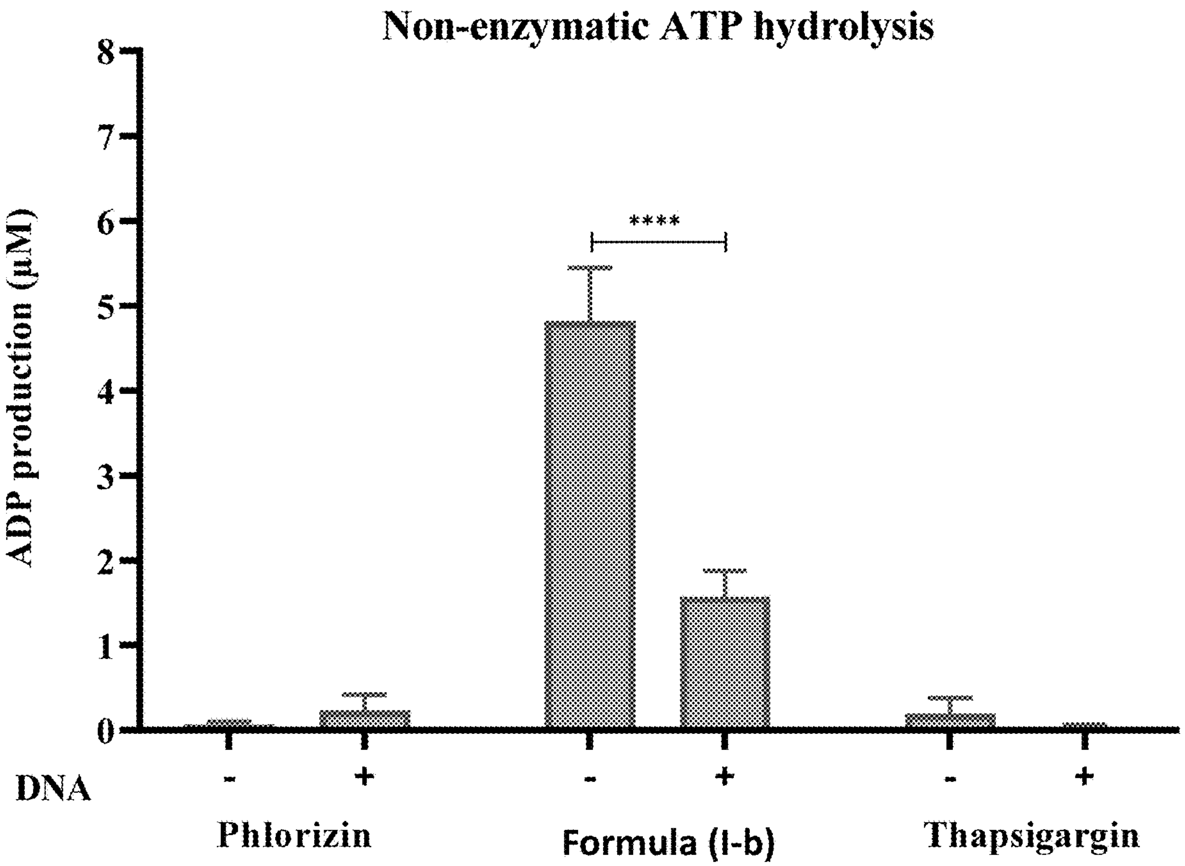
Non-enzymatic ATP hydrolysis
ADP production (μM)
8
7
6
5
4
3
2
1
0
****
DNA
-
+
-
+
-
+
Phlorizin
Formula (I-b)
Thapsigargin

PHARMACEUTICAL COMPOSITION COMPRISING BICYCLIC COMPOUNDS FOR USE AS ENERGY BOOSTERS

TECHNICAL FIELD

The present invention relates to a pharmaceutical composition, specifically to a composition for non-enzymatic catalysis of ATP hydrolysis. More specifically, compounds are bicyclic compounds having a fused bicyclic core structure that are useful in the treatment of disease, conditions, or disorders associated with impaired cellular bioenergetics or for enhancing cellular energy (e.g. by providing an energy boost).

BACKGROUND

In the human body, energy production is a continuous and dynamic process. Under typical circumstances, the body relies on aerobic respiration, a highly efficient mechanism that occurs within the mitochondria of cells. This process uses oxygen to convert glucose, fats, and proteins into adenosine triphosphate (ATP), the molecule that powers nearly all cellular activities. The journey begins with glycolysis, where glucose is broken down into pyruvate in the cytoplasm. Pyruvate then enters the mitochondria and fuels the citric acid cycle, generating electron carriers that drive oxidative phosphorylation, where the electrons from NADH and $FADH_2$ pass through the electron transport chain, generating a proton gradient that powers the bulk of ATP synthesis. This oxygen-dependent pathway yields up to 36-38 ATP molecules per glucose molecule, making it the preferred method during rest and moderate activity.

However, when the body faces conditions such as intense physical exertion, low oxygen availability, fasting, or illness, it shifts to alternative energy pathways. In oxygen-deprived states, anaerobic respiration takes over, converting glucose to lactic acid and producing only 2 ATP per glucose molecule, less efficient but faster. During prolonged fasting or carbohydrate scarcity, the liver initiates gluconeogenesis, synthesizing glucose from non-carbohydrate sources like amino acids and glycerol to maintain blood sugar levels. Simultaneously, fat stores are mobilized through lipolysis, and the liver produces ketone bodies via ketogenesis, which serve as an alternative fuel, especially for the brain.

In extreme cases, the body may even break down muscle proteins to meet energy demands, a process known as protein catabolism. These adaptive responses are tightly regulated by hormones such as insulin, glucagon, cortisol, and adrenaline, ensuring that vital organs like the brain and heart continue to function even under stress. The human body's ability to switch between energy pathways highlights its remarkable resilience and metabolic flexibility.

In the existing prior arts, enzymes like ATPases are required to regulate and facilitate the release of energy from adenosine triphosphate (ATP). Several molecules are known that may trigger indirect mechanisms to activate or deactivate the enzymes by modulating the activity of ATPases or related cellular pathways responsible for ATP hydrolysis—the process through which energy is released in the body. These include: CCCP, BAM15, Nigericin, Gramicidin, Monensin, Thapsigargin, Ionomycin, Forskolin, AICAR, Geldanamycin, Radicicol, 17-AAG, Arimoclomol, Celastrol, MG132, VER-155008, BIIB021, and SNX-2112.

Molecules such as Carbonyl cyanide m-chlorophenyl hydrazone (CCCP) & BAM15 are mitochondrial uncouplers and disrupt the proton gradient across the mitochondrial membrane, forcing cells to burn more fuel to maintain ATP levels. Nigericin, Gramicidin, and Monensin are ionophores that alter ion transport across membranes, affecting cellular energy balance and indirectly influencing ATPase activity. Thapsigargin & Ionomycin modulate calcium signaling, which can impact ATP-dependent calcium pumps and overall energy demand. Forskolin & 5-Aminoimidazole-4-carboxamide ribonucleotide (AICAR) activate signaling pathways such as cAMP and AMPK, which regulate metabolism and mitochondrial biogenesis. Geldanamycin, Radicicol, 17-Allylamino-17-demethoxygeldanamycin (17-AAG, VER-155008), and BIIB021 are Heat Shock Protein 90 (HSP90) inhibitors and affect protein folding and stress responses, which can alter ATP consumption. MG132 is a proteasome inhibitor that impairs protein degradation, indirectly influencing cellular energy usage. Celastrol & Arimoclomol modulate heat shock responses and cellular stress, impacting ATP-dependent chaperone systems.

While these molecules do not directly catalyze ATP hydrolysis or release its chemical energy, they modulate the cellular environment in ways that can accelerate or suppress ATP breakdown, often by influencing the enzymes and pathways involved in ATP hydrolysis.

Certain compounds can trigger mechanisms that indirectly elevate ATP hydrolysis. Chaperone Activators are molecules that target molecular chaperones like Hsp70 and Hsp90, which rely on ATP hydrolysis to assist in protein folding, stabilization, and stress recovery. Valinomycin, a potassium ionophore, disrupts the ionic equilibrium across mitochondrial membranes by selectively transporting $K^+$ ions. Valinomycin indirectly increases ATP hydrolysis by stimulating energy-demanding ion transport processes. Ouabain, at low doses, acts as a stimulator of the $Na^+/K^+$-ATPase activity under specific conditions, enhancing its activity and thereby increasing ATP consumption. Myosin-Actin interactions are central to muscle contraction, where actin-myosin cross-bridge cycling is a major consumer of ATP. Compounds that stimulate muscle contraction or calcium release includes caffeine or ryanodine receptor activators that can enhance this interaction by activating myosin ATPase, leading to indirect increase of ATP hydrolysis.

Nonetheless, these molecules do not directly catalyze ATP hydrolysis. Instead, they act by stimulating or enhancing the activity of ATP-hydrolyzing enzymes (ATPases). Also, their mechanism of action is fundamentally distinct from non-enzyme-mediated hydrolysis. Thus, there are no known molecules that directly increase ATP hydrolysis under standard physiological conditions.

There remains a need for a pharmaceutical composition comprising therapeutic agents or compounds capable of directly catalyzing ATP hydrolysis, specifically through non-enzymatic mechanisms to enhance cellular energy output to treat diseases, conditions or disorders characterized by impaired cellular bioenergetics.

Objectives of the Invention

An objective of the invention is to overcome the limitations of existing formulations by providing therapeutic formulations containing a compound of Formula I configured to modulate cellular energy metabolism, particularly under conditions of impaired bioenergetics.

Another objective of the invention is to provide a pharmaceutical composition comprising the therapeutic compounds of Formula I for non-enzymatic catalysis of ATP hydrolysis, aimed at treating disorders related to impaired bioenergetics, including but not limited to mitochondrial disorders (e.g., Mitochondrial Myopathy, Leigh Syndrome, Mitochondrial Encephalomyopathy, Lactic Acidosis, and Stroke-like episodes (MELAS Syndrome), Kearns-Sayre Syndrome), neurological and muscular conditions (e.g., Chronic Fatigue Syndrome [CFS/ME], Parkinson's Disease, Amyotrophic Lateral Sclerosis [ALS], Multiple Sclerosis [MS]), cardiovascular and metabolic disorders (e.g., Heart Failure, Ischemia/Reperfusion Injury, Diabetes Mellitus), genetic and metabolic diseases (e.g., Pompe Disease, McArdle Disease, Carnitine Deficiency) and the like.

Yet another objective of the invention is to develop a pharmaceutical dosage form comprising the therapeutic compounds of Formula I for administration to subjects in need thereof, wherein the dosage form is configured to efficiently deliver the therapeutic compounds in a manner that promotes non-enzymatic ATP hydrolysis and enhancing bioavailability and therapeutic efficacy.

A further objective of the invention is to provide a method for treating, preventing, or managing diseases, conditions or disorders in which deliberate modulation of cellular bioenergetics offers therapeutic benefit. The method encompasses restoration of intracellular energy balance in settings of pre-existing bioenergetic impairment (such as mitochondrial dysfunction, metabolic syndromes, and neurodegenerative diseases). The invention reestablishes a cellular energy state conducive to the desired clinical outcome. In a preferred embodiment, the method restores intracellular energy balance and mitigates pathological effects associated with ATP deficiency in subjects with bioenergetic impairments. Another objective of invention is to use the composition or dosage form comprising therapeutic compounds of Formula I as chemical catalysts for the direct hydrolysis of adenosine triphosphate (ATP) to adenosine diphosphate (ADP) and inorganic phosphate to facilitate energy production in cells.

An additional object of invention is to use the disclosed dosage forms and compositions to stimulate or restore energy metabolism in cells subjected to physiological stress, proteotoxicity, or metabolic imbalance, through direct or indirect modulation of bioenergetic pathways.

A further objective of the invention is to provide a method of increasing ATP hydrolysis in subjects in need thereof. For example, the method can provide a benefit to the subject in need thereof, such as enhancing or improving cellular energy.

The foregoing and other objects, features, and advantages of the present invention will become readily apparent upon further review of the following overview and description of the preferred embodiment as illustrated in the accompanying drawings.

SUMMARY

This section provides a general summary of the disclosure and is not meant to be a comprehensive disclosure of the full scope of all its features.

The present disclosure is directed towards compounds, including pharmaceutically active agents such as ML367, represented by Formula (I), along with their corresponding dosage forms, pharmaceutical compositions, and use these to directly catalyze ATP hydrolysis through a non-enzymatic mechanism. Without being bound by theory, the claimed compounds can catalyze ATP hydrolysis without recruiting, activating, or otherwise modulating ATP-hydrolyzing enzymes, thus they can be deployed in various therapeutic and non-therapeutic contexts. First, in healthy subjects (for example, athletes, military personnel, or other individuals seeking an energy boost) the disclosed compounds may be administered in an energy-boosting regimen, yielding a perceptible increase in stamina, focus and endurance. Second, in subjects afflicted with genetic, metabolic or acquired disorders characterized by diminished ATP production, or an absence or insufficiency of ATP-hydrolyzing enzymes, the compounds can restore or approximate normal bioenergetic homeostasis by providing a controlled, enzyme-independent route for ATP hydrolysis, thus normalizing cellular energy balance. The observed effects are independent of enzymatic pathways, meaning the compounds do not trigger activation of the enzyme responsible for ATP hydrolysis, nor do they engage any other enzymatic processes.

In accordance with the present invention, disclosed herein is a pharmaceutical composition for non-enzymatic catalysis of ATP hydrolysis, the composition comprising (i) a therapeutically effective amount of a compound of Formula (I) (or a pharmaceutically acceptable salt, co-crystal, polymorph, hydrate, solvate, prodrug, bioisostere, or a stereoisomer thereof);

(ii) a therapeutically effective amount of adenosine triphosphate (ATP); and (iii) at least one pharmaceutically acceptable excipient; wherein Formula (I) is:

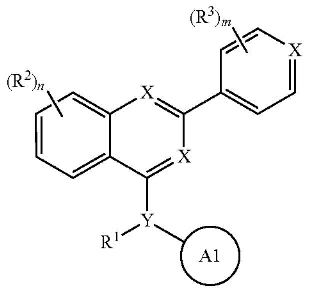

wherein A1 is selected from a group consisting of substituted aryl, unsubstituted aryl, substituted heteroaryl and unsubstituted heteroaryl;

wherein R1 is selected from a group consisting of hydrogen, alkyl, alkenyl, cycloalkyl, haloalkyl and aryl, wherein R2, R3 are each independently selected from a group consisting of alkyl, alkenyl, alkynyl, cycloalkyl, aryl, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl, wherein any of the foregoing moieties is optionally substituted;

wherein Y is —C, —N or —P;

wherein X is independently selected from the group consisting of —C, —N or —P; and wherein m and n are each independently 0, 1, 2, 3 or 4.

In an embodiment, for Formula (I), A1 is substituted aryl, substituted with one or more moieties selected from a group consisting of alkyl, alkenyl, alkynyl, cycloalkyl, aryl, halogen, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl.

In an embodiment, the composition is formulated to promote ATP hydrolysis in the absence of enzymatic activity, and is suitable for administration to a subject in need thereof.

In an embodiment, the composition promotes ATP hydrolysis in the absence or presence of DNA.

In an embodiment, the therapeutically effective amount of the compound of Formula (I) is at a concentration in a range of 1 nM to 10 μM.

In an embodiment, the composition is formulated in a form selected from the group consisting of tablets, capsules, granules, or suspensions.

In an embodiment, the pharmaceutical excipient is selected from the group consisting of binders, disintegrants, lubricants, stabilizers, solubilizers, and pharmaceutically acceptable carrier to enhance bioavailability.

In an embodiment, the pharmaceutical composition further comprises one or more additional therapeutic agents. The additional therapeutic agents may be administered prior to, concurrently with, or subsequently to the administration of the compound of Formula (I) or the pharmaceutical composition comprising the compound of Formula (I).

In an embodiment, the acceptable carrier is selected from solvents, fillers and binders, liposomes and nanoparticles to enhance absorption and bioavailability.

In an embodiment, the composition is configured to non-enzymatically catalyze ATP hydrolysis. In accordance with the present invention, disclosed herein is a pharmaceutical dosage form for administration to a subject, comprising: a therapeutically effective amount of a compound of Formula (I); a therapeutically effective amount of adenosine triphosphate (ATP); and at least one pharmaceutically acceptable excipient, wherein the dosage form is configured to deliver the composition in a manner suitable for promoting non-enzymatic ATP hydrolysis.

In an embodiment, the dosage form is a capsule, the capsule comprising: a first compartment containing the therapeutically effective amount of a compound of Formula (I), or a pharmaceutically acceptable salt, co-crystal, polymorph, hydrate, solvate, prodrug, bioisostere, or a stereoisomer thereof; and a second compartment containing the therapeutically effective amount of adenosine triphosphate (ATP), wherein the first compartment and the second compartment are physically separated within the capsule. In a preferred embodiment, the components in the first compartment and second compartment do not mix until administration. For example, the therapeutically effective amount of a compound of Formula (I) (or a pharmaceutically acceptable salt, co-crystal, polymorph, hydrate, solvate, prodrug, bioisostere, or a stereoisomer thereof) and the therapeutically effective amount of adenosine triphosphate (ATP) do not mix until administration.

In an embodiment, the dosage forms are formulated to exhibit a controlled-release mechanism selected from the group consisting of a sustained-release matrix, an enteric coating, and a polymer-based delivery system.

In an embodiment, the dosage form is selected from the group consisting of a tablet, capsule, transdermal patch, and oral suspension.

In an embodiment, the pharmaceutical excipient is selected from the group consisting of binders, disintegrants, lubricants, or pharmaceutically acceptable carrier to enhance bioavailability and storage conditions.

In an embodiment, the pharmaceutical composition further comprises one or more additional therapeutic agents. The additional therapeutic agents may be administered prior to, concurrently with, or subsequently to the administration of the compound of Formula (I) or the pharmaceutical composition comprising the compound of Formula (I).

In an embodiment, the pharmaceutically acceptable carrier is selected from the group consisting of solvents, fillers and binders, liposomes and nanoparticles to enhance absorption and bioavailability.

In an embodiment, the dosage form is administered as a single-dose regimen or multi-dose protocol, depending on the therapeutic indication.

In accordance with the present invention, disclosed herein is a method of treating or preventing disease, condition or disorder in a subject in need thereof, comprising administering to the subject a therapeutically effective amount of a pharmaceutical dosage form comprising:

(i) a therapeutically effective amount of a compound of Formula (I);

(ii) adenosine triphosphates (ATP); and (iii) at least one pharmaceutically acceptable excipient, wherein the dosage form restores intracellular energy balance and mitigates pathological effects associated with ATP deficiency.

In an embodiment, the disease, conditions or disorders are selected from the group consisting of mitochondrial myopathies, ischemic stroke, chronic fatigue syndrome, neurodegenerative diseases, and other conditions characterized by impaired cellular bioenergetics.

In accordance with the present invention, disclosed herein is a use of composition or dosage form comprising a compound of Formula (I) as a chemical catalyst for the hydrolysis of adenosine triphosphate (ATP) to adenosine diphosphate (ADP) and inorganic phosphate.

In an embodiment, the hydrolysis of ATP occurs in a non-enzymatic manner, facilitated solely by the catalytic activity of the compounds of Formula (I) under physiologically relevant conditions.

In accordance with the present invention, disclosed herein is a method for catalyzing the hydrolysis of adenosine triphosphate (ATP) to adenosine diphosphate (ADP) and inorganic phosphate, the method comprising: contacting a compound of Formula (I) with ATP to form a reaction mixture; adjusting a predefined parameters of the reaction mixture, feasible for non-enzymatic hydrolysis; introducing, optionally, a solvent selected from water, ethanol, dimethyl sulfoxide (DMSO), or mixtures thereof; wherein the compounds catalyze ATP hydrolysis to ADP and inorganic phosphate.

In an embodiment, the hydrolysis of ATP is conducted in the absence of ATP-hydrolyzing enzymes. In an embodiment, the hydrolysis of ATP is conducted in the presence or absence of other molecules, enzymes, inhibitors, or competitors, preferably in the absence of other molecules, enzymes, inhibitors, or competitors.

In an embodiment, the predefined parameters include temperature, pressure, and pH. For example, under physiological conditions representative of the human body.

In accordance with the present invention, disclosed herein is a method of increasing ATP hydrolysis in a subject in need thereof, comprising: administering to the subject a therapeutically effective amount of a compound of Formula (I), or a pharmaceutically acceptable salt thereof, wherein the administration enhances intracellular ATP turnover and promotes the conversion of ATP to ADP and inorganic phosphate for therapeutic modulation of energy metabolism.

In an embodiment, the therapeutically effective amount ranges from 1 nM to 10 μM, and the concentration is selected to achieve therapeutic efficacy while minimizing off-target effects.

Other features, benefits, and advantages of the present invention will be apparent upon a review of the present disclosure, including the specification, abstract, and claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings: FIG. 1 illustrates a graph depicting the non-enzymatic ATP hydrolysis activity of the compound ML367, represented by Formula (I-b), to generate cellular energy both in the presence and absence of DNA.

Definitions

As used in this description and the accompanying claims, the following terms shall have the meanings indicated, unless the context otherwise requires:

As used herein, the singular forms “a”, “an”, and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising”. The transitional terms/phrases (and any grammatical variation thereof) “comprising”, “comprises”, “comprise”, “consisting essentially of”, “consisting”, and “consists” can be used interchangeably.

The term “exemplary” is used herein to mean “serving as an example, instance, or illustration.” Any embodiment described herein as “exemplary” is not necessarily to be construed as preferred or advantageous over other embodiments.

The term “exemplary” is used herein to mean “serving as an example, instance, or illustration.” Any embodiment described herein as “exemplary” is not necessarily to be construed as preferred or advantageous over other embodiments.

The term “bioisostere” refers to a compound or group that possesses near molecular shapes and volumes, approximately the same distribution of electrons, and which exhibits similar physical properties such as hydrophobicity. Bioisostereic compounds affect the same biochemically associated systems as agonists or antagonists and thereby produce biological properties that are related to each other.

The terms “stereoisomer” or “stereoisomers” refer to any enantiomers, diastereomers, or geometrical isomers of the compounds of the Formulae (I), wherever they are chiral. When the compounds of the Formulae (I) and related formulae are chiral, they can exist in racemic or in optically active form. It should be understood that the invention encompasses all stereochemical isomeric forms, including diastereomeric, enantiomeric, and epimeric forms, and mixtures thereof.

As used herein, the term “composition” is intended to encompass a product comprising the specified ingredients in the specified amounts, as well as any product which results, directly or indirectly, from the combination of the specified ingredients in the specified amounts. By “pharmaceutically acceptable,” it is meant that the carrier, diluent, or excipient must be compatible with the other ingredients of the formulation and not deleterious to the recipient thereof.

As used herein, the terms “comprises” or “comprising” are generally used in the sense of include, that is to say, permitting the presence of one or more features or components.

As used herein, the terms “optional” or “optionally” mean that the subsequently described event or circumstance may occur or may not occur, and that the description includes instances where the event or circumstance occurs as well as instances in which it does not. For example, “optionally substituted alkyl” refers to the alkyl that may be substituted, as well as the event or circumstance where the alkyl is not substituted.

The term “pharmaceutically acceptable” means that which is useful in preparing a pharmaceutical composition that is generally safe, non-toxic, and neither biologically nor otherwise undesirable, and includes that which is acceptable for veterinary as well as human pharmaceutical use. These “pharmaceutically acceptable” substances are suitable for use in interacting with bodily tissues without causing excessive irritation, allergic responses, or other complications, commensurate with a reasonable benefit/risk ratio.

The term “pharmaceutically acceptable salt” refers to the salts of the compounds that are pharmaceutically acceptable and that possess the desired pharmacological activity of the parent compound. The pharmaceutically acceptable salts of the compounds of this disclosure include those derived from suitable inorganic and organic acids and bases. Such salts include: salts derived from inorganic bases such as Li, Na, K, Ca, Mg, Fe, Cu, Zn, Al, Mn, comprising their different oxidation states; salts of organic bases such as N,N'-diacetylethylenediamine, 2-dimethylaminoethanol, isopropylamine, morpholine, piperazine, piperidine, procaine, diethylamine, triethylamine, trimethylamine, tripropylamine, tromethamine, choline hydroxide, dicyclohexylamine, metformin, benzylamine, phenylethylamine, dialkylamine, trialkylamine, thiamine, aminopyrimidine, aminopyridine, purine, pyrimidine, spermidine, and the like; chiral bases like alkylphenylamine, glycinol, phenyl glycinol and the like, salts of natural amino acids such as glycine, alanine, valine, leucine, isoleucine, lysine, arginine, serine, threonine, phenylalanine; unnatural amino acids such as D-isomers or substituted amino acids; salts of acidic amino acids such as aspartic acid, glutamic acid; guanidine, substituted guanidine wherein the substituents are selected from nitro, amino, alkyl, alkenyl, alkynyl, ammonium or substituted ammonium salts. Salts may include acid addition salts where appropriate, which are sulphates, nitrates, phosphates, perchlorates, borates, hydrohalides, acetates, tartrates, maleates, citrates, succinates, methanesulfonates, benzoates, salicylates, hydroxynaphthoates, benzenesulfonates, ascorbates, and the like thereof.

The term “pharmaceutically acceptable carrier” as used herein means a pharmaceutically acceptable material, composition, or vehicle, such as a liquid or solid filler, diluent, excipient, solvent, or encapsulating material. Each carrier must be "acceptable" in the sense of being compatible with the other ingredients of the formulation and not injurious to the patient.

The term "polymorph" refers to the crystallization of the same compound, which differs only in the lattice.

As used herein, the terms "prevents", "preventing", "prevention", "arresting", "blocking", "alleviating", "relieving", or "inhibits" refer to a method of preventing or inhibiting the onset of a disease and/or its attendant symptoms or barring a subject from acquiring a disease. As used herein, "prevent", "preventing", "prevention", "arresting", "blocking", "alleviating", "relieving", or "inhibiting" also include delaying the onset of a disease and/or its attendant symptoms and reducing a subject's risk of acquiring a disease.

The terms "solvate" or "solvates" refer to a complex in which the compounds of the Formulae (I) of the present disclosure are a proportionate amount of solvent molecules combined. A specific solvate in which the solvent is water is referred to as a hydrate.

The term "subject" in accordance with the present invention includes, e.g., mammals, such as dogs, cats, horses, rats, mice, monkeys, and humans.

The terms "therapeutically effective amount" or "effective amount" refer to the quantity of the compound of the Formulae (I) disclosed herein that (i) treats or prevents a specific disease, disorder, or condition or syndrome; (ii) reduces, improves, or eliminates one or more symptoms associated with the disease, disorder, or syndrome; or (iii) delays the onset of one or more symptoms of the disease, disorder, or syndrome described herein.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal. In an embodiment, a prodrug has less than 10 percent activity relative to the free or active drug derived or released therefrom. In an embodiment, a prodrug has less than 5 percent activity relative to the free or active drug derived or released therefrom. In an embodiment, a prodrug has less than 1 percent activity relative to the free or active drug derived or released therefrom.

The terms "—S", "—N", "—O", "—P" refer to a sulfur, nitrogen, oxygen, or phosphorus atom, and may include the forms "—S—", "—N—", "—O—", "—P—", "—P=", "—N=" where applicable due to formula structure requirements.

The term "substituted" as used herein refers to substitution with at least one substituent, for example, an alkyl group, an alkenyl group, and an alkynyl group, a cycloalkyl group, and an aryl group As used herein, the term "cycloalkyl" refers to a saturated carbocyclic radical having from 3-8 carbon atoms and includes, for example, cyclopropyl, cyclobutyl, cyclopentyl, cyclohexyl, cycloheptyl, and cyclooctyl.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido, and succinimido groups.

The recitation of a listing of chemical groups in any definition of a variable herein includes definitions of that variable as any single group or combinations of listed groups. The recitation of an embodiment for a variable or aspect herein includes that embodiment as any single embodiment or in combination with any other embodiments or portions thereof.

Unless defined otherwise, all technical and scientific terms used herein have the same meaning as commonly understood by one of ordinary skill in the art to which the disclosure belongs. Although any methods and materials like or equivalent to those described herein may be used in the practice or testing of the present disclosure, the preferred materials and methods are described below.

The present invention pertains to a class of bicyclic compounds, useful in the treatment of disease, conditions, or disorders associated with impaired cellular bioenergetics. In a therapeutic formulation, these scaffolds facilitate the catalysis of adenosine triphosphate (ATP) hydrolysis, thereby enhancing energy production in the body. Said hydrolysis of ATP generates adenosine diphosphate (ADP), inorganic phosphate (Pi), and releases usable energy. The disclosed compounds promote non-enzymatic ATP hydrolysis, thereby facilitating the conversion of chemical energy into a bioavailable form that supports diverse metabolic and catabolic pathways.

In an aspect of the present invention, a pharmaceutical composition comprising a therapeutically effective amount of a compound of Formula (I), or a pharmaceutically acceptable salt, co-crystal, polymorph, hydrate, solvate, prodrug, bioisostere, or a stereoisomer thereof, is disclosed. These compounds confer the ability to induce autohydrolysis of ATP, the primary energy currency of the cell. These compounds accelerate ATP hydrolysis in the absence of enzymes as energy-modulating agents. The compounds are structurally represented as follows:

Formula (I)

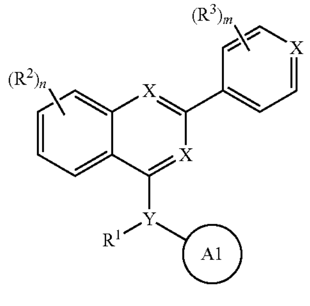

wherein A1 is selected from a group consisting of substituted aryl, unsubstituted aryl, substituted heteroaryl and unsubstituted heteroaryl;

wherein R1 is selected from a group consisting of hydrogen, alkyl, alkenyl, cycloalkyl, haloalkyl and aryl, wherein R2, R3 are each independently selected from a group consisting of alkyl, alkenyl, alkynyl, cycloalkyl, aryl, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl, wherein any of the foregoing moieties is optionally substituted;

wherein Y is —C, —N or —P;

wherein X is independently selected from the group consisting of —C, —N or —P; and wherein m and n are each independently 0, 1, 2, 3 or 4.

In a preferred embodiment, the composition further comprises a therapeutically effective amount of adenosine triphosphate (ATP) and at least one pharmaceutically acceptable excipient.

In a preferred embodiment, A1 is substituted aryl, substituted with one or more moieties selected from a group consisting of alkyl, alkenyl, alkynyl, cycloalkyl, aryl, halogen, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl.

In a further embodiment, the composition having Formula (I) is a therapeutically effective amount of a compound of Formula (I-a):

Formula (I-a)

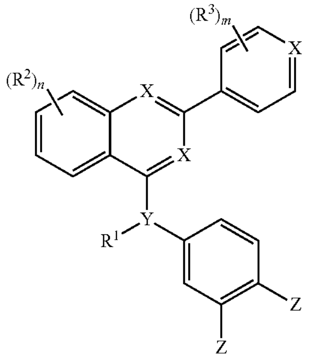

wherein A1 is selected from a group consisting of substituted aryl, unsubstituted aryl, substituted heteroaryl and unsubstituted heteroaryl;

wherein R1 is selected from a group consisting of hydrogen, alkyl, alkenyl, cycloalkyl, haloalkyl and aryl, wherein R2, R3 are each independently selected from a group consisting of alkyl, alkenyl, alkynyl, cycloalkyl, aryl, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl, wherein any of the foregoing moieties is optionally substituted;

wherein Y is —C, —N or —P;

wherein X is independently selected from the group consisting of —C, —N or —P;

wherein m and n are each independently 0 or 1; and wherein Z is a hydrogen, halogen or alkyl.

In a further preferred embodiment, the Formula (I) is a therapeutically effective amount of a compound of Formula I-b:

Formula-Ib (ML367)

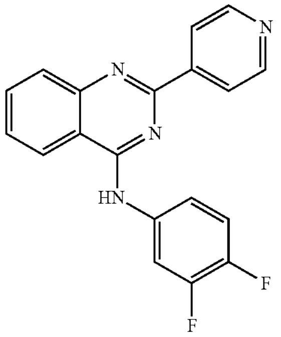

The composition may conveniently be presented in unit dosage form and may be prepared by any method well known in the art of pharmacy. The amount of active ingredient that can be combined with a carrier material to produce a single dosage form will vary depending upon the host being treated and the particular mode of administration. The amount of active ingredient that can be combined with a carrier material to produce a single dosage form will generally be the amount of the compound that produces a therapeutic effect. Generally, out of one hundred percent, this amount will range from about 1 percent to about ninety-nine percent of active ingredients, preferably from about 5 percent to about 70 percent, most preferably from about 10 percent to about 30 percent.

A method of preparing these formulations or compositions includes the step of bringing into association an active compound, such as the compounds of the present invention, with the carrier and, optionally, one or more accessory ingredients. In general, the formulations are prepared by uniformly and intimately bringing into association a compound of the present disclosure with liquid carriers or finely divided solid carriers or both, and then, if necessary, shaping the product. Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated and like factors well known in the medical arts. A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount," is meant the concentration of a compound that is sufficient to elicit the desired therapeutic effect. It is generally understood that the effective amount of the compound will vary according to the weight, sex, age, and medical history of the subject. Other factors that influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art.

In general, a suitable daily dose of an active compound used in the compositions and methods of the disclosure will be that amount of the compound that is the lowest dose effective to produce a therapeutic effect. Such an effective dose will generally depend upon the factors described above.

In a preferred embodiment, the therapeutically effective amount of the compound of Formula (I) is independently at a concentration in a range from 1 nM to 10 μM, wherein the concentration is selected to achieve therapeutic efficacy while minimizing off-target effects.

Exemplary concentrations of the compound of Formula (I) is in range from about 1 nM, 2 nM, 5 nM, 10 nM, 20 nM, 50 nM, 100 nM, 200 nM, 500 nM, 1 μM, 2 μM, 3 μM, 4 μM, 5 μM, 6 μM, 7 μM, 8 μM, 9 μM, and 10 μM. In an embodiment, the dose is about 1.1, 1.2, 1.3, 1.4, 1.5, 1.6, 1.7, 1.8, 1.9, 2.0, 2.5, 3.0, 3.5, 4.0, 4.5.5.0, 5.5, 6.0, 6.5, 7.0, 7.5, 8.0, 8.5, 9.0, 9.5, and 10 μM. In certain embodiments, the concentration of the compound will typically be in the range of about 1 mg/day to about 1000 mg/day per kg body weight of the subject.

In a preferred embodiment, the composition is formulated such that the molar ratio of ATP to the compound of Formula (I) is from about 1:1 to about 1:100. Preferably, the molar ratio is from about 1:1 to about 1:50, from about 1:1 to about 1:40, from about 1:1 to about 1:30, or from about 1:1 to about 1:20. More preferably, the molar ratio is from about 1:2 to about 1:25 or from about 1:5 to about 1:20. Even more preferably, the molar ratio is from about 1:5 to about 1:15, and in particularly preferred embodiments the molar ratio is about 1:10.

The compounds of the present invention can be formulated and administered in a prodrug form. A prodrug is generally defined as a biologically inactive derivative of a parent drug molecule, which is activated by a chemical or enzymatic transformation within the body, which, in the process, involves the release of the active drug. In general, prodrugs comprise functional derivatives of the claimed compounds, which are capable of being enzymatically activated or converted into the more active parent form. Thus, in the treatment methods of the present disclosure, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described. The compounds of the present invention may be obtained from commercial sources or can be prepared by the conventional methods known in the art.

In an embodiment, the composition comprises the pharmaceutically acceptable excipient that are well known in the art and include, selected from the group consisting of wetting agents, emulsifiers, and lubricants, such as sodium lauryl sulfate and magnesium stearate, as well as coloring agents, coating agents, release agents, sweetening, flavoring and perfuming agents, preservatives and antioxidants can also be present in the compositions. In a preferred embodiment, the excipients are selected from a group comprising binders, disintegrants, lubricants, stabilizers, solubilizers, or pharmaceutically acceptable carriers to enhance bioavailability to effect delayed release of an agent or to selectively target one or more cells, tissues, or organs. The composition comprise pharmaceutically acceptable carriers selected from a group comprising (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In a preferred embodiment, the carrier is selected from the group consisting of solvents, fillers and binders, liposomes, and nanoparticles to enhance absorption and bioavailability.

The pharmaceutically acceptable antioxidants are selected from a group comprising (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal-chelating agents, such as citric acid, ethylenediamine tetraacetic acid (EDTA), sorbitol, tartaric acid, phosphoric acid and the like.

In an embodiment, the composition is formulated to non-enzymatically catalyze ATP hydrolysis.

In an embodiment, composition is in the form of a capsule, the capsule comprising: a first compartment containing the therapeutically effective amount of a compound of Formula (I), or a pharmaceutically acceptable salt, co-crystal, polymorph, hydrate, solvate, prodrug, bioisostere, or a stereoisomer thereof; and a second compartment containing the therapeutically effective amount of adenosine triphosphate (ATP), wherein the first compartment and the second compartment are physically separated within the capsule. In a preferred embodiment, the components in the first compartment and second compartment do not mix until administration. For example, the therapeutically effective amount of a compound of Formula (I) (or a pharmaceutically acceptable salt, co-crystal, polymorph, hydrate, solvate, prodrug, bioisostere, or a stereoisomer thereof) and the therapeutically effective amount of adenosine triphosphate (ATP) do not mix until administration.

In another embodiment, the pharmaceutical composition may be formulated as tablets, pills, powders, granules, capsules, suspensions, liquids for internal use, emulsions, syrups, aerosols, or sterile injectable solutions. Depending on the intended use, the composition can be administered to a subject by any of a number of routes of administration including, for example orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin or as an eye drop). The compound may also be formulated for inhalation. In yet another embodiment, the compound may be simply dissolved or suspended in sterile water.

The pharmaceutical composition is administered by any appropriate route, selected from a group comprising orally, parenterally, topically, or rectally. It will be appreciated that the preferred route may vary, for example, the condition of the recipient of the compound and the disease to be treated. In certain embodiments, the extract may be especially suitable for the preparation of pharmaceuticals for intravenous administration, such as intravenous injection or infusion, provided that it does not contain components with serum-precipitating and/or haemagglutinating properties which disturb such an application. The extract may therefore be provided in the form of ampoule preparations, which are directed to intravenous administration. In still other embodiments, the method comprises systemic administration of a subject composition to a subject. The pharmaceutical compositions intended for human administration, particularly via invasive routes of administration such as injection or implantation, where delivery circumvents transport or diffusion across an epithelial barrier, are formulated as aqueous solutions that are pyrogen-free or substantially pyrogen-free.

In an aspect, the present invention discloses a pharmaceutical dosage form for administration to a subject for promoting non-enzymatic ATP hydrolysis. The administering of the pharmaceutical dosage form comprises a therapeutically effective amount of a compound having Formula (I), a therapeutically effective amount of adenosine triphosphate (ATP), a pharmaceutically acceptable carrier, and at least one pharmaceutically acceptable excipient. Said dosage form is formulated to deliver the composition in a manner suitable for promoting non-enzymatic ATP hydrolysis. The dosage forms are formulated to exhibit a controlled-release mechanism selected from the group consisting of a sustained-release matrix, an enteric coating, and a polymer-based delivery system. Said dosage form is selected from the group consisting of a tablet, capsule, transdermal patch, and oral suspension. The dosage form is administered as a single-dose regimen or multi-dose protocol, depending on the therapeutic indication.

In an embodiment, the dosage form is a capsule, the capsule comprising: a first compartment containing the therapeutically effective amount of a compound of Formula (I), or a pharmaceutically acceptable salt, co-crystal, polymorph, hydrate, solvate, prodrug, bioisostere, or a stereoisomer thereof; and a second compartment containing the therapeutically effective amount of adenosine triphosphate (ATP), wherein the first compartment and the second compartment are physically separated within the capsule. In a preferred embodiment, the components in the first compartment and second compartment do not mix until administration. For example, the therapeutically effective amount of a compound of Formula (I) (or a pharmaceutically acceptable salt, co-crystal, polymorph, hydrate, solvate, prodrug, bioisostere, or a stereoisomer thereof) and the therapeutically effective amount of adenosine triphosphate (ATP) do not mix until administration.

If desired, the effective daily dose of the active compound may be administered as one, two, three, four, five, six, or more sub-doses administered separately at appropriate intervals throughout the day, optionally, in unit dosage forms. In yet another embodiment of the present disclosure, the active compound may be administered two or three times daily. In preferred embodiments, the active compound will be administered once daily.

In an aspect, the present invention discloses a method of treating or preventing a disease, condition, or disorder in a subject in need thereof. The method comprises administering to the subject a therapeutically effective amount of a pharmaceutical dosage form comprising a therapeutically effective amount of compounds having Formula (I), adenosine triphosphates ATPs, and at least one pharmaceutically acceptable excipient. The dosage form restores intracellular energy balance and mitigates pathological effects associated with ATP deficiency.

In an embodiment, the disease, conditions, or disorders are selected from the group consisting of mitochondrial myopathies, ischemic stroke, chronic fatigue syndrome, neurodegenerative diseases, and other conditions characterized by impaired cellular bioenergetics.

In an aspect, the present invention discloses the use of a composition or dosage form comprising compounds having Formula I as chemical catalysts for the hydrolysis of adenosine triphosphate (ATP) to adenosine diphosphate (ADP) and inorganic phosphate.

In an embodiment, the hydrolysis of ATP occurs in a non-enzymatic manner, facilitated solely by the catalytic activity of the compounds of Formula (I) under physiologically relevant conditions.

In an aspect, the present invention discloses a method for catalyzing the hydrolysis of adenosine triphosphate (ATP) to adenosine diphosphate (ADP) and inorganic phosphate. The method comprises contacting the compounds of Formula (I) with ATP to form a reaction mixture. Adjusting a predefined parameter of the reaction mixture, feasible for non-enzymatic hydrolysis. Followed by introducing, optionally, a solvent selected from water, ethanol, dimethyl sulfoxide (DMSO), or mixtures thereof. Said compounds catalyze ATP hydrolysis to ADP and inorganic phosphate, in the absence of an ATP-hydrolyzing enzyme.

In a preferred embodiment, the predefined parameters include temperature and pH.

In an aspect, the present invention discloses a method of increasing ATP hydrolysis in a subject in need thereof. The method comprises administering to the subject a therapeutically effective amount of compounds of Formula (I) or a pharmaceutically acceptable salt thereof. The administration enhances intracellular ATP turnover and promotes the conversion of ATP to ADP and inorganic phosphate for therapeutic modulation of energy metabolism.

In an embodiment, the method comprises a therapeutically effective amount of the compound of Formula (I) independently at a concentration in a range from 1 nM to 10 μM, wherein the concentration is selected to achieve therapeutic efficacy while minimizing off-target effects.

Exemplary concentrations of the compound of Formula (I) is in range from about 1 nM, 2 nM, 5 nM, 10 nM, 20 nM, 50 nM, 100 nM, 200 nM, 500 nM, 1 μM, 2 μM, 3 μM, 4 μM, 5 μM, 6 μM, 7 μM, 8 μM, 9 μM, and 10 μM. In an embodiment, the dose is about 1.1, 1.2, 1.3, 1.4, 1.5, 1.6, 1.7, 1.8, 1.9, 2.0, 2.5, 3.0, 3.5, 4.0, 4.5.5.0, 5.5, 6.0, 6.5, 7.0, 7.5, 8.0, 8.5, 9.0, 9.5, and 10 μM. In certain embodiments, the concentration of the compound will typically be in the range of about 1 mg/day to about 1000 mg/day per kg body weight of the subject.

The compositions and methods of the present disclosure are utilized to treat a subject in need thereof. In certain embodiments, the subject is a mammal such as a human or a non-human mammal. When administered to an animal, such as a human, the composition or the compound is preferably administered as a pharmaceutical composition comprising the compositions and methods of the present disclosure are useful for treating a subject in need thereof. In certain embodiments, the subject is a mammal, such as a human or a non-human mammal. When administered to a subject, the compound or composition is preferably delivered in the form of a pharmaceutical composition.

Experimental studies demonstrate that ML367 releases energy in the presence of DNA, with the release increasing several folds in the absence of DNA. These compounds represent a unique class capable of promoting energy release by catalyzing the non-enzymatic hydrolysis of adenosine triphosphate (ATP). The observed increase in ATP hydrolysis and consequent energy release is significant and highlights their potential as energy-boosting agents.

EXAMPLES

Example 1—Non-Enzymatic ATP Hydrolysis Assay

Three compounds, Phlorizin, ML367 (a compound of Formula (I)), and Thapsigargin, were obtained from MedChemExpress and dissolved in dimethyl sulfoxide (DMSO) to prepare stock solutions at a final concentration of 10 mM. To evaluate ATP hydrolysis activity, a luminescence-based assay detecting ADP production following ATP hydrolysis was employed (ADP-Glo Assay, Promega). Reaction mixtures were prepared containing 5 nM RSC complex, 20 mM Tris (pH 8.0), 50 mM KCl, 5 mM $MgCl_2$, 5% glycerol, 0.1 mg/mL BSA, 1 mM DTT, 10 ng/μL salmon sperm DNA (Thermo Scientific), 0.5 mM or 1 mM test compound, and 0.1 mM ATP. For non-enzymatic ATP hydrolysis, the assay was conducted in the absence of the RSC complex, both in the presence and absence of DNA. Following incubation for 20 minutes at 30° C., ADP-Glo Reagent and ADP-Glo Max Detection Reagent were added in accordance with the manufacturer's instructions. Luminescence was measured using a TECAN Infinite M200 Pro microplate reader. ADP concentrations were calculated by correlating luminescence values to a standard curve prepared according to the kit protocol. All reactions were performed in triplicate.

FIG. 1 illustrates a graph depicting the non-enzymatic ATP hydrolysis activity of the three compounds both in the presence and absence of DNA. The error bars in the graph indicate the standard error of the mean (SEM). Asterisks (****) denote results that are statistically significant compared to the DNA-containing control at a p-value<0.001, wherein the p-value represents the probability of obtaining the observed results by chance.

Unexpectedly, the compound of Formula (I) exhibited differential activity in comparison to the other compounds. In the presence of DNA, the compound of Formula (I) induced an unexpectedly high rate of ATP hydrolysis, and in the presence of DNA, hydrolysis activity is even higher by several folds. Without limitation to theory, this effect may result from binding interactions between the compounds and DNA, thereby modulating the availability of free compounds for ATP hydrolysis.

The ability of the claimed compounds to increase ATP hydrolysis translates into enhanced cellular energy availability. These are examples such as improved physical and cognitive performance, enhanced muscle function and recovery, accelerated cellular repair and regeneration, maintenance of mitochondrial health, improved endurance, faster post-exercise recovery, increased resistance to fatigue, and better adaptation to metabolic stress, and several more. Furthermore, modulation of ATP hydrolysis at controlled levels may be beneficial in protecting cells from stress.

The non-enzymatic hydrolysis enabled by the present invention accelerates the release of energy in response to immediate physiological demands. This mechanism simplifies cellular machinery by eliminating the need for the synthesis and regulation of complex ATPase enzymes, thereby potentially reducing genetic and metabolic overhead. Additionally, the invention enhances stability under extreme conditions where enzymatic proteins may become denatured. It facilitates instant energy availability and ensures a consistent energy release, minimizing bottlenecks typically caused by enzyme dependency.

The present disclosure, now being generally described, it will be more readily understood by reference to the following examples, which are included merely for purposes of illustration of certain aspects and embodiments of the present disclosure and are not intended to limit the present disclosure in any way.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

What is claimed is:

1. A pharmaceutical dosage form for catalyzing adenosine triphosphate (ATP) hydrolysis, the dosage form comprising:

a pharmaceutical composition comprising:

i) a therapeutically effective amount of a compound of Formula (I), or a pharmaceutically acceptable salt, or a stereoisomer thereof;

ii) a therapeutically effective amount of adenosine triphosphate (ATP); and iii) at least one pharmaceutically acceptable excipient;

a first compartment containing the therapeutically effective amount of a compound of Formula (I), or a pharmaceutically acceptable salt, or a stereoisomer thereof; and a second compartment containing the therapeutically effective amount of adenosine triphosphate (ATP);

wherein the first compartment and the second compartment are physically separated such that the components in the first compartment and second compartment do not mix until administration to a subject, thereby enhancing catalysis of adenosine triphosphate (ATP) hydrolysis;

wherein Formula (I) is:

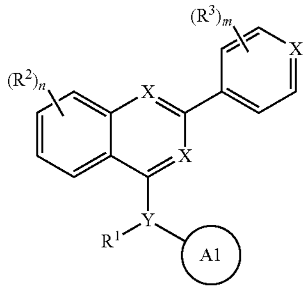

wherein A1 is selected from a group consisting of unsubstituted aryl, substituted heteroaryl, unsubstituted heteroaryl, and substituted aryl, wherein the substituted aryl is substituted with one or more moieties selected from a group consisting of alkyl, alkenyl, alkynyl, aryl, halogen, heterocycloalkyl, heteroaryl, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyl, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl;

wherein R1 is selected from a group consisting of hydrogen, alkyl, alkenyl, cycloalkyl, haloalkyl, and aryl;

wherein R2, R3 are each independently selected from a group consisting of alkyl, alkenyl, alkynyl, cycloalkyl, aryl, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyi, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl, wherein any of the foregoing moieties is optionally substituted;

wherein Y is —C, —N or —P;

wherein X is independently selected from the group consisting of —C, —N or —P; and wherein m and n are each independently 0, 1, 2, 3 or 4.

2. The pharmaceutical dosage form of claim 1, wherein A1 is substituted aryl, substituted with one or more moieties selected from a group consisting of alkyl, alkenyl, alkynyl, aryl, halogen, heterocycloalkyl, heteroaryl, hale, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyl, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl.

3. The pharmaceutical dosage form of claim 1, wherein the compound of Formula (I) is a compound of Formula (Ia) or a pharmaceutically acceptable salt, or a stereoisomer thereof:

Formula (I-a)

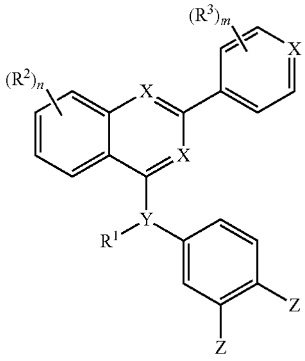

wherein R1 is selected from a group consisting of hydrogen, alkyl, alkenyl, cycloalkyl, haloalkyl and aryl, wherein R2, R3 are each independently selected from a group consisting of alkyl, alkenyl, alkynyl, cycloalkyl, aryl, heterocycloalkyl, heteroaryl, halo, haloalkyl, haloalkoxy, aryloxy, alkanoyloxy, hydroxy, alkoxy, cycloalkyloxy, heterocylalkyloxy, alkanoyl, aroyl, arylalkyl, alkylaryl, heteroarylalkyl, alkylheteroaryl, amino, alkylamino, arylamino, arylalkylamino, cycloalkylamino, heterocycloalkylamino, alkanoylamino, aroylamino, aralkanoylamino, thiol, alkylthio, arylthio, arylalkylthio, cycloalkylthio, heterocycloalkylthio, alkylthiono, arylthiono, arylalkylthiono, alkyl sulfonyl, arylsulfonyl, arylalkylsulfonyl, sulfonamido, nitro, cyano, carboxy, alkoxycarbonyl, carbamido, and carbamyl, wherein any of the foregoing moieties is optionally substituted;

wherein Y is —C, —N or —P;

wherein X is independently selected from the group consisting of —C, —N or —P;

wherein m and n are each independently 0 or 1; and wherein Z is a hydrogen, halogen or alkyl.

4. The pharmaceutical dosage form of claim 1, wherein the compound of Formula (I) is a compound of Formula (I-b) or a pharmaceutically acceptable salt or a stereoisomer thereof;

wherein Formula (I-b) is:

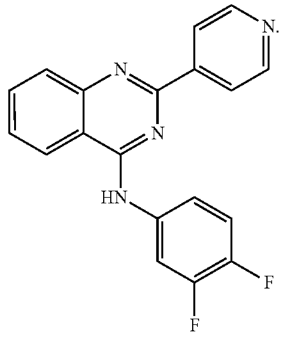 [SMILES: Fc1ccc(Nc2nc(-c3ccncc3)nc3ccccc23)cc1F]

5. The pharmaceutical dosage form of claim 1, wherein the therapeutically effective amount of the compound of Formula (I) is at a concentration in a range of 1 nM to 10 μM.

6. The pharmaceutical dosage form of claim 1, wherein the pharmaceutical excipient is selected from the group consisting of binders, disintegrants, lubricants, stabilizers, solubilizers and acceptable carrier.

7. The pharmaceutical dosage form of claim 1, further comprising one or more additional therapeutic agents.

8. The pharmaceutical dosage form of claim 1, wherein the dosage form is selected from the group consisting of tablets, capsules, granules, and suspensions.

9. The pharmaceutical dosage form of claim 1, wherein the dosage form promotes non-enzymatic ATP hydrolysis following administration to a subject.

10. The pharmaceutical dosage form of claim 1, wherein the dosage form is a capsule.

11. The pharmaceutical dosage form of claim 1, wherein the dosage form is selected from the group consisting of tablets, pills, powders, granules, capsules, suspensions, liquids for internal use, emulsions, syrups, aerosols, and sterile injectable solutions.

12. A method of treating a disease, condition or disorder in a subject associated with ATP deficiency comprising:

administering to the subject a therapeutically effective amount of a pharmaceutical dosage form according to claim 1, wherein the pharmaceutical dosage form restores intracellular energy balance and mitigates pathological effects associated with ATP deficiency.

13. The method according to claim 12, wherein the disease, condition, or disorder is selected from the group consisting of mitochondrial myopathies, ischemic stroke, chronic fatigue syndrome, neurodegenerative diseases.

14. A method of increasing adenosine triphosphate (ATP) hydrolysis in a subject in need thereof, comprising:

administering to the subject a pharmaceutical dosage form according to claim 1, wherein the administration enhances intracellular ATP turnover and promotes the hydrolysis of ATP for modulation of energy and/or for therapeutic use.

15. The method of claim 14, wherein the therapeutically effective amount of the compound of Formula (I) is at a concentration in a range of 1 nM to 10 μM.

16. The method of claim 12, wherein administering comprises a single-dose regimen.

17. The method of claim 12, wherein the administering comprises a multi-dose protocol.

* * * * *